US010495572B2

(12) United States Patent
Krätschmer et al.

(10) Patent No.: US 10,495,572 B2
(45) Date of Patent: Dec. 3, 2019

(54) METHOD FOR DETERMINING A MEASURED QUANTITY CORRELATED WITH AN EXTINCTION, AND CORRESPONDING SENSOR ARRANGEMENT

(71) Applicant: Endress+Hauser Conducta GmbH+Co. KG, Gerlingen (DE)

(72) Inventors: Thilo Krätschmer, Gerlingen (DE); Ralf Bernhard, Stuttgart (DE); Matthias Grossmann, Vaihingen-Enz (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 15/820,566

(22) Filed: Nov. 22, 2017

(65) Prior Publication Data
US 2018/0156729 A1 Jun. 7, 2018

(30) Foreign Application Priority Data
Dec. 7, 2016 (DE) .................. 10 2016 123 650

(51) Int. Cl.
*G01N 21/59* (2006.01)
*G01N 21/51* (2006.01)
*G01N 21/03* (2006.01)

(52) U.S. Cl.
CPC .......... *G01N 21/59* (2013.01); *G01N 21/51* (2013.01); *G01N 21/0303* (2013.01); *G01N 2201/062* (2013.01)

(58) Field of Classification Search
CPC .. G01N 21/51; G01N 21/59; G01N 2201/062; G01N 21/0303

USPC .................................................. 356/432–448
See application file for complete search history.

(56) References Cited

U.S. PATENT DOCUMENTS

| 3,912,393 A | * | 10/1975 | Hossom | G01N 1/38 |
| | | | | 250/265 |
| 4,257,708 A | | 3/1981 | Fukuda | |
| 5,713,352 A | * | 2/1998 | Essenpreis | G01N 21/49 |
| | | | | 600/407 |
| 2003/0025909 A1 | * | 2/2003 | Hallstadius | A23L 3/003 |
| | | | | 356/436 |

(Continued)

FOREIGN PATENT DOCUMENTS

DE 69422669 T2 8/2000
DE 60133002 T2 2/2009

OTHER PUBLICATIONS

Search Report for German Patent Application No. 10 2016 123 650.0, German Patent Office, dated Jul. 28, 2017, 7 pp.

*Primary Examiner* — Tri T Ton
(74) *Attorney, Agent, or Firm* — Kelly J. Smith; PatServe

(57) ABSTRACT

A method is disclosed for determining a measured quantity, correlated with an extinction, in a medium, including the steps: radiation of light into the medium and measurement of the extinction after a first path length; radiation of light into the medium and measurement of the extinction after a second path length, wherein the first path length differs from the second path length; and determination of the measured quantity correlated with the extinction using the extinction after first path length and extinction after second path length. Additionally disclosed is a sensor arrangement for execution of the method.

10 Claims, 4 Drawing Sheets

(56) References Cited

U.S. PATENT DOCUMENTS

2009/0257064 A1* 10/2009 Tkachuk .................. G01J 3/42
356/453
2010/0007888 A1    1/2010 Glover
2012/0140228 A1    6/2012 Bernhard et al.
2014/0301756 A1* 10/2014 Gijsbrechts .......... G03G 15/104
399/249

* cited by examiner

METHOD FOR DETERMINING A MEASURED QUANTITY CORRELATED WITH AN EXTINCTION, AND CORRESPONDING SENSOR ARRANGEMENT

CROSS-REFERENCE TO RELATED APPLICATION

The present application is related to and claims the priority benefit of German Patent Application No. 10 10 2016 123 650.0, filed on Dec. 7, 2016, the entire contents of which are incorporated herein by reference.

TECHNICAL FIELD

The present disclosure relates to a method for determining a measured quantity correlated with an extinction. The present disclosure further relates to a sensor arrangement for implementing the method.

BACKGROUND

One measured quantity correlated with extinction is a concentration, for example. Optical sensors for determining a concentration of a substance in a medium often operate with wavelengths of ultraviolet (UV), visible (VIS), near-infrared (NIR), and/or middle-infrared (MIR) light. An extinction measurement is thereby usually implemented. In the following, the problem shall be described using the measured quantity of the concentration, but analogously occurs for additional measured quantities correlated with extinction.

The measurement principle for determining concentration is based upon the Lambert-Beer law. A linear dependency between the extinction of light and the concentration of a substance to be measured exists for low and medium concentrations, with the formula:

$$E = \log\left(\frac{I_o}{I}\right) = \varepsilon \cdot c \cdot OPL,$$

where E is the extinction, $I_0$ is the intensity of the incident light, I is the intensity of the transmitted light, $\varepsilon$ is the extinction coefficient, c is the concentration, and OPL is the optical path length, viz., the path by which the radiated light penetrates through the medium to be measured. In this regard, see also FIG. 1. The intensity $I_0$ may be determined via a reference measurement. At higher concentrations, this linear dependency no longer applies.

A light source 1 sends radiation through optical window 2 into the medium 5. The radiation remaining after passage through the medium 5 is measured at the detector 3, often after passing through a filter 4. The light is thereby converted by a photodiode into photoelectric current. The final conversion of the determined extinction into the concentration takes place by means of a mathematical model, e.g., an association table, in an associated measuring transducer (not depicted).

The extinction has several different causes. On the one hand, there is the scattering at particles located in the medium, and, on the other hand, there is the absorption of the radiation in the medium and at the particles. As additional causes, diffraction and reflection, by this measurement principle, play a subordinate and negligible role.

If the extinction is measured as described above, the proportions of absorption and scattering cannot be separated, and a generally valid determination of the concentration of a substance to be determined is not possible. A separate model is required for each medium. The medium to be measured (sewage sludge, for example) is a member of class of similar media (i.e., various sludges) that, however, vary in their composition and therefore in their ratio of absorption to scattering. If only the extinction is measured, this ratio is plugged as a constant into the model, which is why it is also valid only for a specific substance. Problems may thereby occur. If the composition of the medium changes from system to system, a different model is required for each system. After initialization, the model must be adapted. This is, for one thing, complicated, and not always possible with continuously running systems. If the process medium changes over time (for example, summer to winter), the model must be adapted in turn, or a switch between different models must take place.

SUMMARY

The present disclosure is based upon the aim of creating a universal method for determining a measured quantity correlated with extinction, which measured quantity is independent of measurement location and environmental conditions.

The aim is achieved by a method comprising the steps: radiation of light into the medium and measurement of the extinction after a first path length; radiation of light into the medium and measurement of the extinction after a second path length, wherein the first path length differs from the second path length; and determination of the measured quantity correlated with the extinction using the extinction after first path length and extinction after second path length.

If two path lengths are now used, or if the extinction is determined from two different path lengths, a measured quantity correlated with the extinction may thus be determined definitely from the two different extinctions especially even when the medium is unknown. Moreover, the method may also be applied in measurement fields in which there is no linear correlation between extinction and measured quantity to be determined.

In one embodiment, a model correlates the extinction after first path length and extinction after second path length to the measured quantity correlated with the extinction. A universal model is thus specified that is independent of environmental conditions and measurement location.

In one embodiment, the measured quantity correlated with the extinction is absorption, scattering, concentration, or turbidity, and a separate model is used for each of these measured quantities correlated with the extinction. Each of these measured quantities may thus be determined independently of one another. Since absorption and scattering are essentially responsible for the extinction, given knowledge of the one, the respective other may be determined. For an unknown medium and an unknown target range of the measured quantity to be determined, it is not possible (except for the dependency between absorption and scattering that was described in the preceding sentence), with knowledge of one measured quantity, to determine an additional measured quantity without adjustment. With use of two path lengths, and using a model separately for each measured quantity, wherein the respective model takes into account the extinction of both path lengths, the corresponding measured quantity may be determined definitely.

The aim is further achieved by a sensor arrangement that is designed to execute a method as described above. For this, the sensor arrangement comprises at least a light source for radiating light into the medium, and at least one detector for measuring extinction. Either at least two light sources or two detectors are arranged, so that it can be ascertained whether light has been directed via the first or second optical path length. In one embodiment, the arrangement comprises an actuator that diverts light to the one or the other path, or shades one path.

In one embodiment, the sensor arrangement comprises a housing that comprises first and second path lengths. Only one housing is thus necessary; all required components, such as light source(s), detector(s), lens(es), etc., are thereby accommodated in the housing and therefore protected from the medium.

In one embodiment, the sensor arrangement comprises a first light source for radiating light in the direction of the first path length, wherein the sensor arrangement comprises a second light source for radiating light in the direction of the second path length, wherein the sensor arrangement comprises a first detector for measuring the extinction after the first path length, and wherein the sensor arrangement comprises a second detector for measuring the extinction after the second path length. This design is relatively simple to produce, and also to service.

In one embodiment, the light source or light sources is/are designed as (an) LED(s).

In one embodiment, the measurement of the extinction after the first path length takes place after radiation of light of a first wavelength by means of a first LED, and the measurement of the extinction after the second path length takes place after radiation of light of a second wavelength by means of a second LED.

In one embodiment, the first and second wavelengths are thereby the same. In one embodiment, infrared light is radiated.

In one embodiment, an additional detector is associated with each light source or light sources, which additional detector is designed to detect intensity changes in the light source or light sources. Symptoms of aging of the LED, changes in the characteristics of the LED due to temperature influences, or general deviations in desired properties of the LED may be detected with the aid of the additional detector.

In one embodiment, the sensor arrangement is designed as a solid content sensor.

BRIEF DESCRIPTION OF THE DRAWINGS

The present disclosure is explained in greater detail with reference to the following figures. These show.

In the figures, the same features are marked with the same reference characters.

DETAILED DESCRIPTION

Figure 1:
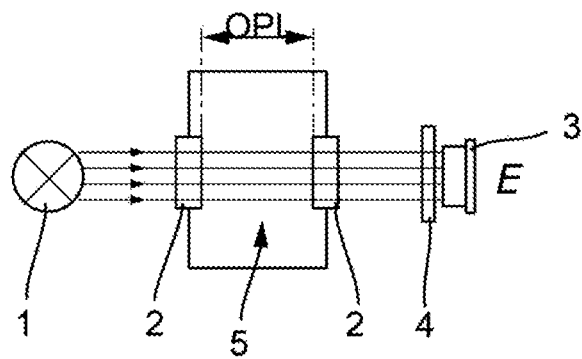
FIG. 1 shows a schematic of a conventional sensor arrangement.
Figure 2A:
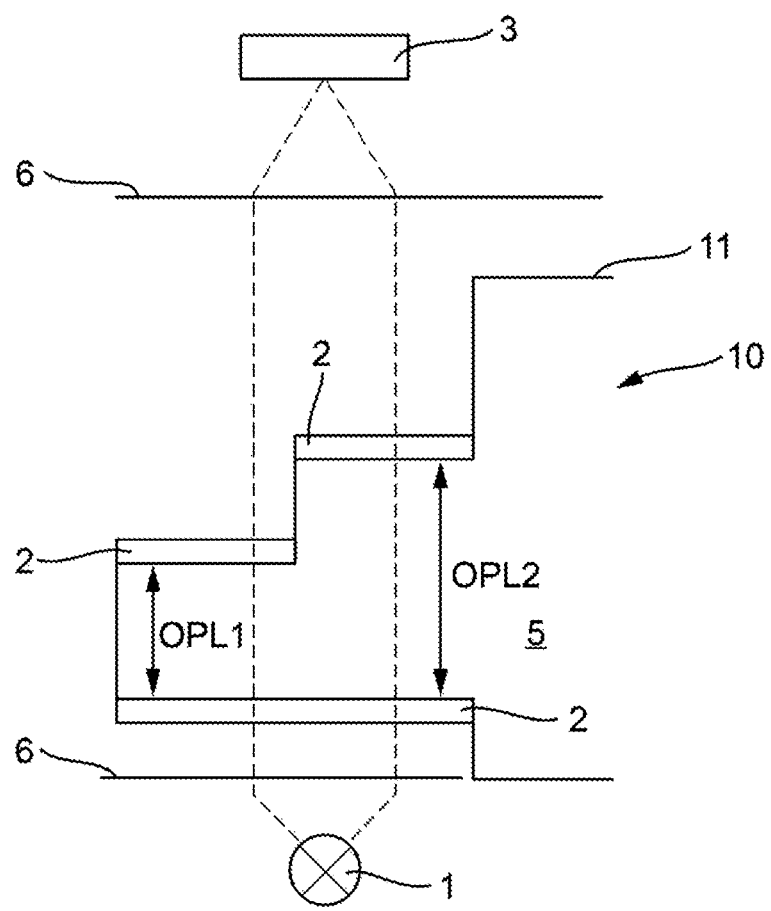
FIGS. 2A and 2B show a schematic overview of the sensor arrangement of the present disclosure in two embodiments.
Figure 2B:
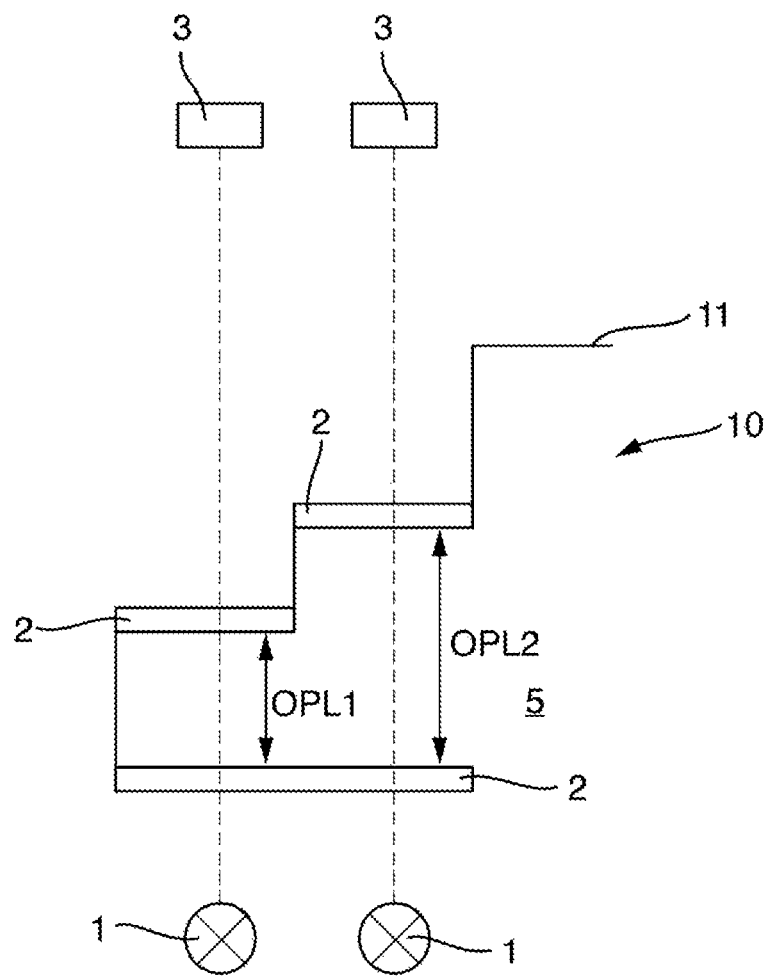

The claimed sensor arrangement has reference character 10 and is depicted in FIGS. 2A and 2B. In principle, the arrangement is similar to that of the prior art (see FIG. 1); therefore, only the differences are discussed here. Not shown in FIG. 1 are lenses or other optical elements 6 which enable a divergence, focusing, linearization, parallelization, shadowing, or deflection of the light.

The depicted windows 2 are designed as optical widows for instance, made of either glass or plastic.

A significant difference to the prior art is that the claimed sensor arrangement 10 comprises two optical path lengths OPL1 and OPL2, wherein these are different from one another. FIG. 2A shows an embodiment having a light source 1 and a detector 3. FIG. 2B shows an embodiment having two light sources 1 and two detectors 3, one each per optical path. For the claimed method, either of two completely different sensors may be used, as long as the respective optical paths OPL1 and OPL2 are different. Alternatively, the two light sources 1 and/or detectors 3 may be arranged within a sensor. The light sources 1 and detectors 3 are arranged within a housing 11.

In one embodiment, the light sources 1 emit infrared light, wherein these are designed as light-emitting diodes (LEDs). In principle, LEDs may be used that emit different wavelengths. In one embodiment, the wavelengths are identical.

In one embodiment, to each LED 1 an additional detector is assigned that detects intensity changes of the LED is associated with each LED 1. This intensity change may be caused by aging or temperature fluctuations. If an LED 1 no longer has the desired properties, it must be replaced.

A measured quantity correlated with extinction, e.g., the concentration of a substance in medium 5, may be determined with the sensor arrangement 10 for instance, also the solid concentration. Additional measured quantities correlated with extinction, such as absorption, scattering, and turbidity, can likewise be determined. In the following, the concentration is initially discussed.

Figure 3:
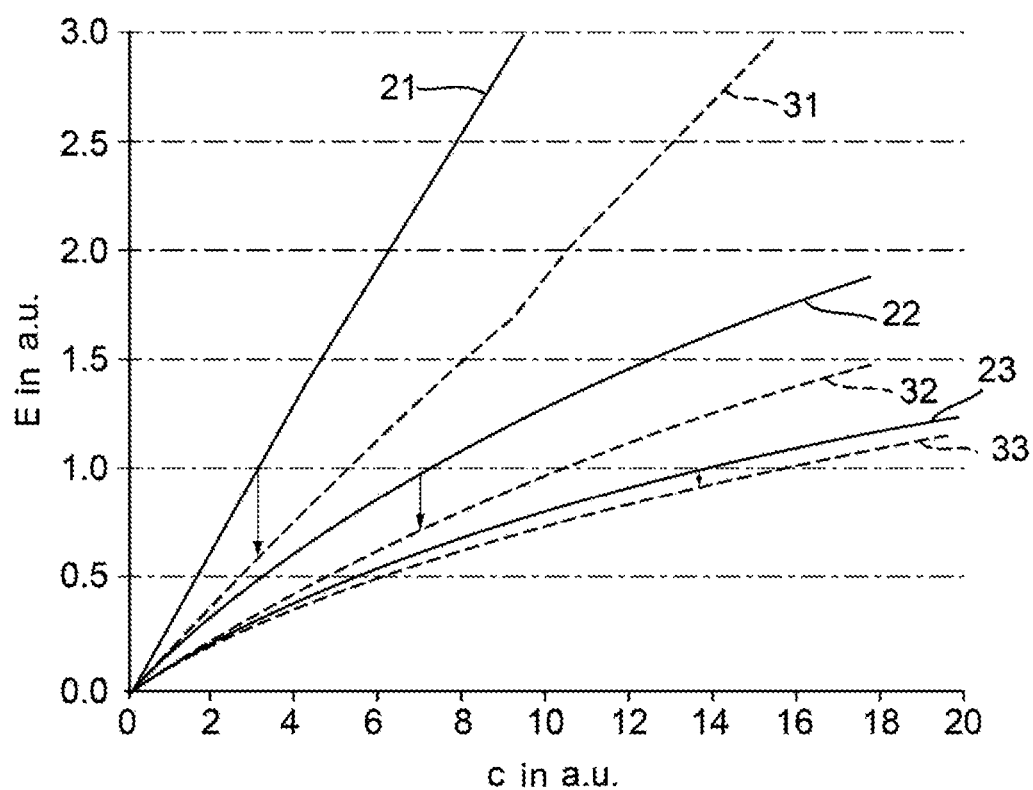
FIG. 3 shows a model that can determine the concentration from the extinction in arbitrary units (a.u.)

The correlation of concentration and extinction is nonlinear, and is different for different media and optical path lengths, which is presented in FIG. 3. FIG. 3 shows a model that maps the extinction E to the concentration c. Both are presented in arbitrary units a.u. For this, the sensor arrangement 10 also comprises a processing unit, e.g., a measuring transducer or by means of a processing unit directly in the sensor, with which this calculation can be performed. For this, the model is stored in a memory in the processing unit. In FIG. 3, three media (solid lines 21 and 31, 22 and 32, 23 and 33) and two optical path lengths (solid and dashed line) are thereby depicted. In the following, the claimed method shall therefore be explained in conjunction with FIG. 3.

If an extinction of 1.0 (see in this regard the solid lines 21, 22, 23) is measured at a first of the path lengths, depending upon the medium, a different concentration results, viz., approximately 3, 7, or 14 g/L in FIG. 3. The mapping of extinction to concentration is thus not definite, since the medium or its composition is unknown. If the value of the extinction of a second path length is additionally known (see dashed lines 31, 32, 33; in the example, thus approximately 0.6, 0.75, or 0.9), an association is thus definite. This model is also stored in the processing unit and is calculated accordingly.

Figure 4:
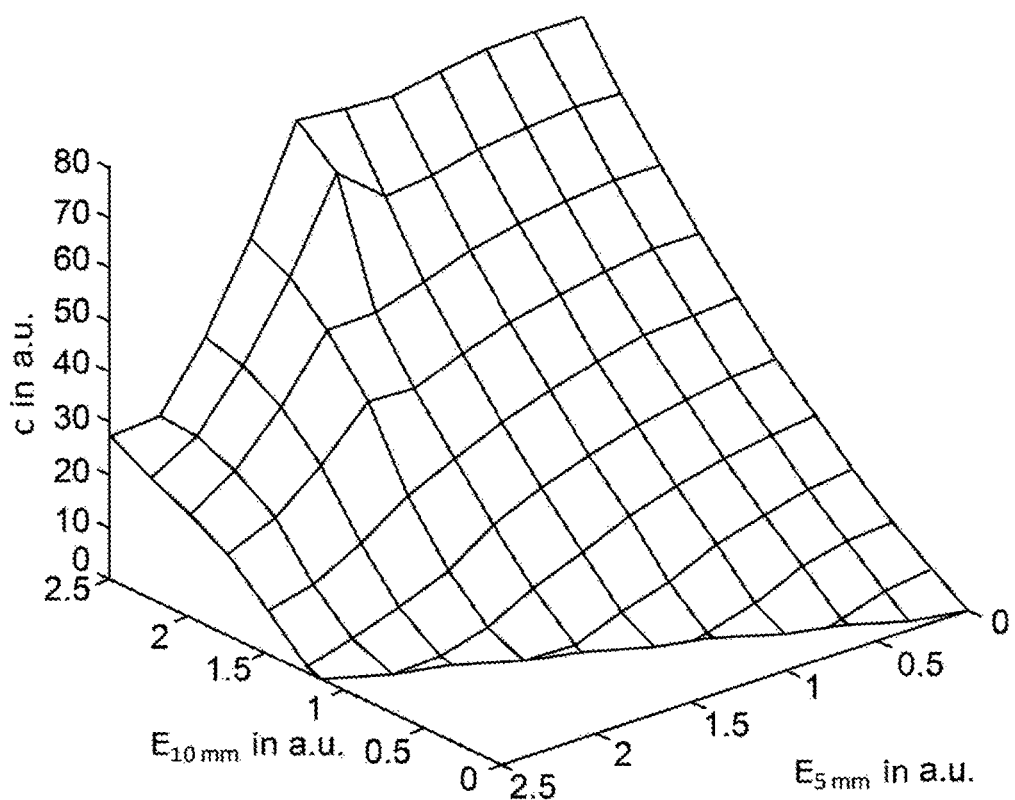
FIG. 4 shows a two-dimensional characteristic diagram of the extinction given two path lengths, relative to the concentration in arbitrary units (a.u.).

FIG. 4 shows its expansion, i.e., no discrete curves, but rather a two-dimensional characteristic diagram. This thus corresponds to a two-dimensional model. On the x-axis or y-axis, the extinctions $E_{5\ mm}$ and $E_{10\ mm}$ are listed at two different path lengths, viz., 5 mm and 10 mm. The z-axis shows the concentration associated with the respective extinctions at different path lengths.

The concentration may thus be determined definitely, independently of the medium and independently of the value range.

Additional models for the determination of the absorption, scattering, and turbidity may be created, corresponding to the model for the concentration. These are also stored in the processing unit. Since a model may be stored for each of the four measured quantities, these can be determined independently of one another. The entire extinction thereby essentially includes the absorption and scattering.

It is possible to determine the absorption and scattering via the use of varying optical path lengths.

The invention claimed is:

1. A method for determining a measured quantity in a medium based on a first light extinction value and a second light extinction value, comprising the steps:
   radiating light into the medium along a first straight optical path and measuring a first light extinction value corresponding to the first straight optical path;
   radiating light into the medium along a second straight optical path and measuring a second light extinction value corresponding to the second straight optical path, wherein a length of the first straight optical path differs from a length of the second straight optical path; and
   determining the measured quantity based on the first light extinction value and the second light extinction value;
   wherein a universal model separately correlates each of the first light extinction value and the second light extinction value to the measured quantity, wherein the universal model is independent of environmental conditions and measurement location.

2. The method of claim 1, wherein the measured quantity is absorption, scattering, concentration, or turbidity, and a different universal model is used for each measured quantity.

3. A sensor arrangement for determining a measured quantity in a medium based on a first light extinction value and a second light extinction value, the sensor arrangement comprising:
   at least one light source embodied to radiate light into the medium along a first straight optical path and a second straight optical path, wherein a length of the first straight optical path differs from a length of the second straight optical path;
   at least one detector embodied to measure the first light extinction value corresponding to the first straight optical path and to measure the second light extinction value corresponding to the second straight optical path; and
   a processor unit configured to determine the measured quantity based on the first light extinction value and the second light extinction value;
   wherein a universal model separately correlates each of the first light extinction value and the second light extinction value to the measured quantity, wherein the universal model is independent of environmental conditions and measurement location.

4. The sensor arrangement of claim 3, further comprising a housing that includes the first straight optical path and the second straight optical path.

5. The sensor arrangement of claim 3, wherein the at least one light source includes a first light source configured to radiate light in a direction of the first straight optical path and a second light source configured to radiate light in a direction of the second straight optical path,
   wherein the at least one detector includes a first detector configured to measure the first light extinction value corresponding to the first straight optical path and a second detector configured to measure the second light extinction value corresponding to the second straight optical path.

6. The sensor arrangement of claim 3, wherein the at least one light source is a light-emitting diode.

7. The sensor arrangement of claim 3, further comprising an additional detector associated with the at least one light source, the additional detector configured to detect intensity changes in the at least one light source.

8. The sensor arrangement of claim 3, wherein the sensor arrangement is embodied as solid content sensor.

9. The sensor arrangement of claim 1, wherein the steps of radiating light into the medium along the first straight optical path and radiating light into the medium along the second straight optical path include emitting light from a light source at a constant intensity.

10. The method of claim 1, wherein each of the first straight optical path and the second straight optical path have a predetermined length.

* * * * *